(12) United States Patent
Hasse et al.

(10) Patent No.: US 9,346,727 B2
(45) Date of Patent: May 24, 2016

(54) PROCESS FOR THE PRODUCTION OF PURE METHYLAL

(71) Applicant: Ineos Paraform GmbH & Co. KG, Mainz (DE)

(72) Inventors: Hans Hasse, Kaiserslautern (DE); Jan-Oliver Drunsel, Kaiserslautern (DE); Jakob Burger, Kaiserslautern (DE); Ulrich Schmidt, Mainz (DE); Mario Renner, Mainz (DE); Sergej Blagov, Mainz (DE)

(73) Assignee: Ineos Paraform GmbH & Co. KG (DE)

( * ) Notice: Subject to any disclaimer, the term of this patent is extended or adjusted under 35 U.S.C. 154(b) by 0 days.

(21) Appl. No.: 14/135,916

(22) Filed: Dec. 20, 2013

(65) Prior Publication Data

US 2014/0187823 A1    Jul. 3, 2014

Related U.S. Application Data

(63) Continuation of application No. 13/884,317, filed as application No. PCT/EP2011/069779 on Nov. 9, 2011, now abandoned.

(30) Foreign Application Priority Data

Nov. 9, 2010 (EP) .................................... 10190581

(51) Int. Cl.
*C07C 41/56* (2006.01)
*C07C 41/09* (2006.01)
*B01D 3/14* (2006.01)
*C07C 41/58* (2006.01)
*B01D 3/00* (2006.01)

(52) U.S. Cl.
CPC ................ *C07C 41/09* (2013.01); *B01D 3/009* (2013.01); *B01D 3/143* (2013.01); *C07C 41/56* (2013.01); *C07C 41/58* (2013.01)

(58) Field of Classification Search
CPC . C07C 41/56; C07C 41/58; B01J 2219/00006
USPC ......................................................... 568/594
See application file for complete search history.

(56) References Cited

U.S. PATENT DOCUMENTS

| 4,385,965 | A | 5/1983 | Muller et al. |
| 6,015,875 | A | 1/2000 | Smith, Jr. et al. |
| 6,379,507 | B1 | 4/2002 | Satoh et al. |
| 7,301,055 | B2 * | 11/2007 | Hoffmockel et al. ......... 568/472 |
| 2006/0129000 | A1 | 6/2006 | Goring et al. |

FOREIGN PATENT DOCUMENTS

CN        101597117 A    12/2009

OTHER PUBLICATIONS

International Search Report for PCT/EP2011/069779 mailed Dec. 20, 2011.

* cited by examiner

*Primary Examiner* — Sikarl Witherspoon
(74) *Attorney, Agent, or Firm* — Drinker Biddle & Reath LLP

(57) ABSTRACT

The invention relates to a continuous process to make and isolate methylal by reacting formaldehyde and methanol with an acid catalyst under at least partial formation of methylal and water, to form a mixture M2 comprising formaldehyde, methanol, methylal, and water, separating the said mixture M2 in a distillation column B into three distinct product streams, one being a distillate taken from the column head BH which is rich in methylal, one taken from the column bottom stream BB being almost pure water, and one taken from the side of the column B below the reaction zone which stream is rich in methanol, characterised in that the ratio of the amount of substance of methanol to the amount of substance of formaldehyde in the mixture M1 is at least 3 mol/mol, and to an apparatus to be used with this process.

11 Claims, 1 Drawing Sheet

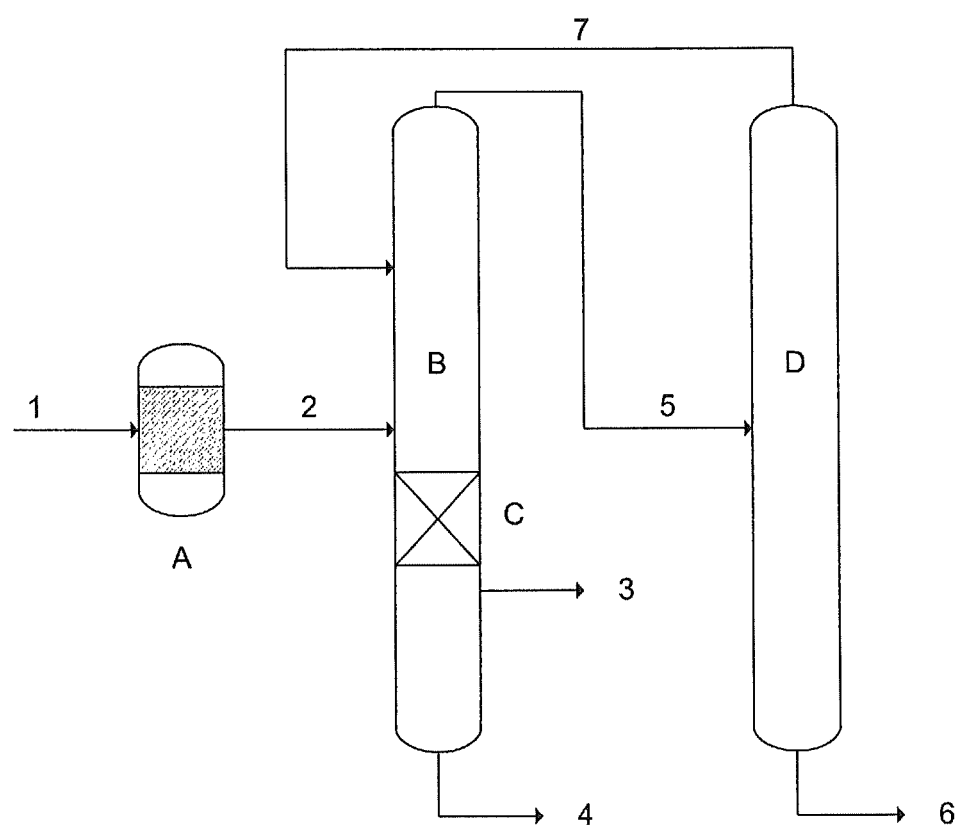

PROCESS FOR THE PRODUCTION OF PURE METHYLAL

CROSS-REFERENCE TO RELATED APPLICATIONS

This application is a continuation of Ser. No. 13/884,317 filed on May 9, 2013 (incorporated herein by reference), which is a national stage application (under 35 U.S.C. 371) of PCT/EP2011/069779 filed Nov. 9, 2011 Nov. 9, 2011, which claims benefit of European application 10190581.8 filed Nov. 9, 2010.

SUBJECT OF THE INVENTION

This invention relates to a process for the production of pure methylal, also referred to as formaldehyde dimethylacetal, dimethylformal or dimethoxymethane, from a mixture of formaldehyde and methanol. It also relates to a two-step process wherein the first step, methanol and formaldehyde are reacted to form methylal, and in the second step, the reaction mixture which comprises at least methylal, and unreacted methanol and formaldehyde, is separated by distillation to provide substantially pure methylal. It further relates to an apparatus to be used for this process.

BACKGROUND OF THE INVENTION

In "Houben—Weyl, Methoden der organischen Chemie", vol. VI/3, Oxygen Compounds 1, Part 3 [1965], page 207, a process is described to produce a mixture of methylal and methanol with a mass fraction of approximately 8% of the latter in an industrial process using iron trichloride as catalyst. Separation of the remaining methanol from this mixture is difficult as this composition corresponds to an azeotrope.

Several processes have been described in the literature to recover pure methylal from reaction mixtures also comprising methanol.

In a paper by Volkov and Ivanov (Vysokomol. Soedin. 8 (8) [1966], pages 1459 to 1461) and a further paper by Vinokurov (Nauch. Doklady Vysskei Shkoly Lesoinzhener. Delo. No. 4 [1958], pages 193 to 195), a purification process for methylal is described comprising reacting the methanol present with metallic sodium. According to Ullmann's Encyclopaedie der Technischen Chemie, third edition, vol. 3, page 15 et seq., methanol can also be removed by extraction with concentrated aqueous calcium chloride solution, and by subsequent drying of the methylal.

In US 2006/0129 000 A1, a process for the synthesis of methylal from methanol and formaldehyde is described where an additional extractant has to be used which is fed to the rectifying section of a distillation column, water or an aqueous formaldehyde solution being preferred. An additional extractive rectification step is then needed to remove the added water, ethylene glycol being mentioned as the product of choice.

In U.S. Pat. No. 6,015,875, a process from making acetals is described where a mixture of alcohols and aldehydes is fed into a reaction zone in a column, and a mixture of alcohol and acetal is collected from the head stream of the column. This reaction is not complete, and the recovered distillate comprising the acetal has still a large amount of unreacted alcohol, 26.5% in the example. This mixture is further concentrated in a second column, to yield an overhead containing mass fractions of 0.2% of dimethyl ether, 3.5% of methanol, and 95.5% of methylal.

U.S. Pat. No. 6,379,507 B1 relates to a process for producing methylal, where a distillation column is fed in different heights with the efflux of at least four solid acid-filled reactors, the reactors being fed with liquid collected in bottom of the distillation column. Despite the large efforts taken in apparatus and ancillary equipment such as pumps, counter-current feeding of aqueous formalin solution, and addition of defoamer to the top portion of the column, a mass fraction of methylal of not more than 98% was reached.

From CN 1015 7117 A, a method to treat formaldehyde-containing industrial waste water has been known which involves adding methanol to the waste water, transferring the mixture to a reactor while simultaneously adding catalyst, and separating the excess methanol in a rectification tower. This process is merely designed to remove formaldehyde from the water, nothing can be learned about the yield and purity of methylal which is separated in this process from water as a mixture of methylal and methanol.

In the U.S. Pat. No. 4,385,965, a process for recovery of methylal from methanol-methylal mixtures is described which involves two rectifying columns operated at different pressures, with the pressure difference being at least 8 bar (0.8 MPa). The second column is typically run at from 9 bar to 30 bar (0.9 MPa to 3 MPa), preferably at from 10 bar to 15 bar (1 MPa to 1.5 MPa); the need to employ high pressure columns should be avoided. This patent does not describe the separation of aqueous formaldehyde solutions, nor does it teach the formation of methylal. Specially prepared mixtures of methanol and methylal, in examples 1, 2, and 3, and in example 4, a mixture of water, methylal, methanol, and a minor quantity of methyl formiate (corresponding to a mass fraction of 0.8%. in the mixture) were used.

Additional auxiliary substances or special equipment have to be used in these processes which makes these processes complicated and expensive.

Methylal has gained interest as fuel additive, solvent, and as adjuvant in certain polymers.

SUMMARY OF THE INVENTION

Thus, it is an object of the invention to provide a process for the preparation of highly pure methylal without admixture of other components such as methanol. A further object of this invention is to provide a process which generates a waste water stream which does not have a mass fraction in excess of 1% of total organic substances, with a mass fraction of methanol of less than 0.01%, and a mass fraction of formaldehyde of less than 1%, thereby leading to a tolerable level of organic impurities in the waste water stream, and consequently, a low value of COD (chemical oxygen demand). The process desired should lead to high yields of methylal, and avoid substantial losses of methanol, nor require the use of foreign substances.

The invention therefore provides a process to make and isolate methylal by a first acid-catalysed reaction of formaldehyde and methanol in a reactor, preferably in an aqueous environment, a first distillation step in a rectifying column B equipped with a reaction zone C in its lower half, comprising a catalyst bed, where the product stream of the first reaction step which comprises methylal, water, and unconverted methanol and unconverted formaldehyde is fed to the column B above the reaction zone C within column B, and separated in the column B into three distinct product streams, one being a distillate taken from the column head BH which has a mass fraction of more than 90% of methylal, one taken from the column bottom stream BB being almost pure water, and one taken from the side of the column B below the reaction zone C which stream is rich in methanol. The product stream taken from the column head BH which consists almost exclusively of methylal and a mass fraction of less than 10% of methanol is then optionally fed to the side of a rectifying column D, where a mixture of methylal and methanol having a mass fraction of methylal of between 70% and 95% is recovered from the column top, and highly pure methylal is recovered as sump product from the bottom of the column D, in a purity in excess of 99.5%.

In the context of this invention,

"rich in methylal" refers to a mixture having a mass fraction of methylal of at least 80%, preferably, at least 85%, and particularly preferred, at least 90%, "almost pure water" refers to a mixture having a mass fraction of water of at least 95%, preferably, at least 98%, and particularly preferred, at least 99%, "rich in methanol" refers to a mixture having a mass fraction of methanol of at least 80%, preferably, at least 85%, and particularly preferred, at least 90%, and "pure methylal" and "consisting almost exclusively of methylal" refer to mixtures having a mass fraction of methylal of at least 98%, preferably, at least 99%, and particularly preferred, at least 99.5% which latter is also referred to as "highly pure methylal".

High purity and good conversion can be achieved if the ratio of the amount of substance of methanol n(MeOH) and the amount of substance of formaldehyde n(FA) is at least 3 mol/mol, i. e. at least 150% of the stoichiometric ratio.

A BRIEF DESCRIPTION OF THE FIGURE

FIG. 1 is a schematic diagram of an arrangement of columns for conducting the process according to the invention where both reactor A and a reaction zone C within column B are present, and a second column D is present with the product stream collected at the head of column D is recirculated to column B.

DETAILED DESCRIPTION OF THE PREFERRED EMBODIMENTS

An object of the invention is a continuous process to make and isolate methylal by reacting a mixture M1 comprising formaldehyde and methanol with an acid catalyst under at least partial formation of methylal and water, to form a mixture M2 comprising formaldehyde, methanol, methylal, and water separating the said mixture M2 in a distillation column B into three distinct product streams, one being a distillate taken from the column head BH which is rich in methylal, one taken from the column bottom stream BB being almost pure water, and one taken from the side of the column B below the reaction zone C which stream is rich in methanol, optionally, feeding the product stream taken from the column head BH which consists almost exclusively of methylal, and further comprises a mass fraction of less than 10% of methanol to the side of a rectifying column D which is operated with a pressure which is higher than the pressure in column B, where a stream comprising a mixture of methylal and methanol having a mass fraction of methylal of between 70% and 95% is recovered from the column top DH, and pure methylal is recovered as sump product stream from the bottom DB of the column D, in a purity in excess of 99.5%, characterised in that the ratio of the amount of substance of methanol to the amount of substance of formaldehyde in the mixture M1 is at least 3 mol/mol, and the reaction of formaldehyde and methanol to form mixture M2 under at least partial formation of methylal and water is conducted in a separate reactor A, and the mixture M2 is fed to the side of the distillation column B to a feed point in a height corresponding to between 40% and 70% of the effective height of column B, or a mixture comprising formaldehyde and methanol is fed to the side of the distillation column B to a feed point in a height corresponding to between 40% and 70% of the effective height of column B, which column B is additionally equipped with a reaction zone C which is located between the said feed point and the bottom of the said column B, in which reaction zone at least partial conversion to methylal occurs.

Separating the exit streams 3 and 4 of the distillation column B leads to the unexpected advantage that methanol is excluded from the stream 4 exiting the bottom of column B, which can therefore be directly fed into the waste water treatment facility. "Exclusion of methanol" means that the mass fraction of methanol in the exit stream 4 is preferably below 100 mg/kg.

In a first preferred embodiment, the reaction of methanol and formaldehyde is conducted in a reactor A, wherein formaldehyde is preferably used in the form of an aqueous solution, having a mass fraction of dissolved formaldehyde (also referred to as "concentration" in this application) of preferably at least 10%, more preferred from 20% to 80%, and practically, from 30% to 70%. Concentrations of up to 95% are possible at temperatures of about 120° C.

The reactor A may be a stirred reactor, or a preferably tubular reactor. The latter is more favourable particularly if a fixed bed catalyst is used. The reaction is preferably conducted at a temperature of from 40° C. to 80° C. Higher reaction temperatures accelerate the reaction, and also allow to use higher formaldehyde concentrations. Depending on the residence time and temperature, this reaction usually does not go to completion. Preferably, the conversion, based on the consumption of formaldehyde in reactor A, is at least 80%, particularly preferably, at least 85%, an especially preferred, at least 90% .

In a second preferred embodiment, a mixture M1 of formaldehyde and methanol is directly fed to the distillation column B, above a reaction zone which comprises an acid fixed bed catalyst, i. e., with no pre-reaction in a reactor A.

In a third preferred embodiment, both a reactor A and a reaction zone C in the column B are used. This setup is favourable to complete the reaction, and to minimise the amount of unreacted formaldehyde, together with the choice of the ratio of the amounts of substance of formaldehyde and methanol as detailed infra.

The reaction between formaldehyde and methanol, which includes formation of a hemiacetal from one molecule each of formaldehyde and methanol, and in the second step, formation of an acetal by etherification of a hemiacetal with a further methanol molecule under elimination of water, is catalysed by acids in both steps. These acids are preferably Brønsted acids, i. e. molecules or ions that can donate a hydrogen cation, or proton. Useful Bronsted acids are sulphuric acid, methane sulphonic acid, and phosphoric acid, as well as acids fixed to a surface of a solid material referred to as fixed bed catalysts, particularly ion exchange resins in their protonated form, most commonly bearing sulphuric acid or sulphonic acid groups, and optionally, also other acid groups. These acid fixed bed catalysts offer the advantage that the catalyst does not have to be separated from the product streams.

In the third preferred embodiment, the product mixture from reactor A which comprises unreacted formaldehyde, unreacted and excess methanol, methylal formed in the reaction, and water, is fed to the distillation column B preferably in mid-height, i. e. preferably at between 40%; and 60%, of the effective height of column B. Below this feed point, in the region of from 20% to 55%; of the effective height of the column B, is a reaction zone referred to as reaction zone C which is equipped with an acid catalyst on a solid carrier, preferably an ion exchange resin in its protonated form as described supra.

It is important in the context of this invention to employ methanol in excess to the stoichiometric ratio, the ratio of the amount of substance of methanol to the amount of substance of formaldehyde in methylal being 2 mol/mol if stoichiometric. The range for the ratio of the amount of substance of methanol to the amount of substance of formaldehyde employed in the process according to the invention is at least 3 mol/mol, preferably between 4 mol/mol and 15 mol/mol, particularly preferred between 5 mol/mol and 12 mol/mol. A range of the ratio of the amount of substance of methanol to the amount of substance of formaldehyde that has been particularly useful in the context of the invention, with a mass fraction of impurities in the methylal obtained by the process of the invention being not more than 0.15%, and the mass fraction of methanol in the methylal obtained being not more than 0.05% was between 5.5 mol/mol and 10 mol/mol.

The distillate from column B is an azeotrope having a mass fraction of methylal of at least 90%, depending on the temperature and pressure conditions in column B. It is therefore preferred to subject this azeotrope to a further distillation step in column D operated under a higher pressure than the first column, into a methanol-containing stream of materials which includes a large mass fraction of methylal, e. g., between 70% and 90%, and pure methylal with a purity corresponding to a mass fraction of methylal of at least 99.5% is obtained as the sump product. The methanol-containing compound stream is then withdrawn from column D at the column head DH, and preferably recirculated to column B. This stream is preferably fed into column B at a height corresponding to between 60% and 90% of its effective height, but always above the feed point of the mixture of methanol or formaldehyde which is fed into column B in the second embodiment, or above the feed point where the mixture M2 emerging from the reactor A is fed into column B, in the first and third embodiments.

Preferably, the pressure in column D is at least 100 kPa higher than that of column B. Column B is preferably operated at atmospheric pressure (101.3 kPa) or up to 500 kPa. In a particularly preferred embodiment, the pressure of column D is at least 150 kPa higher than that of column B, and more preferred, at least 200 kPa higher.

The product stream isolated from the bottom BB of column B has no methanol, and no methylal, both chemicals being below the limit of detection, and a low residual amount of formaldehyde corresponding to a mass fraction of less than 1.0%, and in the experiments, always lower than 0.9%.

The product stream 3 which has a mass fraction of usually at least 90% of methanol, and between 4% and 8% of water, can preferably be used as feed stream for a formaldehyde production unit. Particularly preferred for such use is the so-called BASF process as described in Ullmann's Encyclopedia of Industrial Chemistry, 5th Edition, vol. All, page 619 et seq., using silver crystal catalysts as this process starts from a mixture of methanol and water.

Further preferred process variants and embodiments are described in the dependent claims.

A still further object of the invention is an apparatus designed for this process, which comprises a reaction vessel A equipped with a fixed bed catalyst, a distillation column B having two lateral feed inlets, and one lateral outlet, and a head and a sump outlet, optionally, a further distillation column D having one lateral feed inlet, and a head and a sump outlet. It is preferred that the distillation column B has a reaction zone C equipped with a fixed bed catalyst. This fixed bed catalyst preferably comprises an ion exchange resin in its protonated form. A particularly preferred embodiment has a tubular reactor as the reactor A.

BRIEF DESCRIPTION OF THE DRAWING

FIG. 1 is a schematic diagram of an arrangement of columns for conducting the process according to the invention where both reactor A and a reaction zone C within column B are present, and a second column D is present with the product stream collected at the head of column D is recirculated to column B. Stream 1, also referred to as mixture M1, is a mixture of an aqueous solution of formaldehyde, and methanol. Stream 2, also referred to as mixture M2, is the at least partially reacted product exiting the reactor A, and fed into the column B at half-height. Column B has an outlet for stream 3 which comprises methanol, and a mass fraction of about 6% of water, and stream 4 is almost pure water that goes to the waste water treatment unit. From the top of column B, stream 5 is taken off which is an azeotrope of methylal and methanol (mass fractions of about 93% and 7%, respectively), and fed to a pressure column D where the azeotrope is broken into highly pure methylal as stream 6, the sump product, and a mixture of methylal and methanol as stream 7 which is fed back to column B.

The invention is further explained in the following example:

EXAMPLE

A mixture (1) of 1400 kg/h of methanol and 350 kg/h of an aqueous formaldehyde solution having a mass fraction of dissolved formaldehyde of 50%, with a feed temperature of 50° C. was continuously fed into a tubular reactor equipped with a fixed bed catalyst (ion exchange resin with sulphonic acid groups) operated at 70° C. and an average residence time of twelve minutes. The resulting product mixture (2) with a temperature of 70° C. was then fed at half-height (50%) into a distillation column B having a bottom temperature of 100° C. and operated at atmospheric pressure (101.3 kPa). The distillation column B was equipped with a reaction zone covering a height of 10% of the effective column height, located between 35% and 45% of the effective height of the column, counted from the bottom, and having therein a plurality of perforated plates coated with ion exchange resin in its protonated form. At an outlet located at 30% of the effective height, a stream (3) of 1121 kg/h was taken out with a temperature of 68° C. From the bottom of the column, a sump stream (4) of 203 kg/g of almost pure water was discharged. The product stream (5) of 1100 kg/h collected at the top of the column had a temperature of 40° C. and comprised a mass fraction of about 93% of methylal with methanol as the only major by-product. This stream (5) was fed into a side inlet located at 50% of the effective height of the second distillation column D which was operated at a pressure of 350 kPa. A stream (6) of 426 kg/h of pure methylal having a mass fraction of methylal of 99.9% was taken from the sump. This corresponds to a yield based on formaldehyde of 95.9%. The stream (7) of 675 kg/h which has about 89% of methylal and 11% of methanol is recirculated to column B, at the effective height of 75% of this column.

Measured data on these streams are compiled in the following table:

|  |  | Stream | | | | | | |
|---|---|---|---|---|---|---|---|---|
|  |  | 1 | 2 | 3 | 4 | 5 | 6 | 7 |
| Temperature | °C. | 50 | 70 | 68 | 100 | 40 | 88 | 86 |
| Mass Stream | kg/h | 1750 | 1750 | 1121 | 203 | 1101 | 426 | 675 |
| FA | mass | 10 | 0.8 | 0.03 | 0.8 | 0 | 0 | 0 |
| W | fraction in % | 10 | 14.9 | 5.9 | 99.2 | 0.03 | 0.06 | 0.01 |
| MeOH |  | 80 | 61.6 | 94 | 0 | 6.9 | 0.04 | 11.2 |
| Mal |  | 0 | 22.7 | 0.1 | 0 | 93.1 | 99.9 | 88.8 |

FA: formaldehyde
W: water
MeOH: methanol
Mal: methylal
The numbers of streams are those given in parentheses in the text of the example, and correspond to those of the FIGURE.

It was found that the purity of methylal may be further increased if column D is operated at higher pressure. High yield, low waste water COD, and high purity of the methylal make this improved process attractive.

The invention claimed is:

1. A continuous process to make and isolate methylal which comprises
   reacting in a reactor A a mixture M1 comprising formaldehyde and methanol with an acid catalyst under at least partial formation of methylal and water, to form a mixture M2 comprising formaldehyde, methanol, methylal, and water, and feeding the said mixture M2 to the side of a distillation column B to a feed point in a height corresponding to between 40% and 70% of the effective height of column B,
   separating the said mixture M2 in the said distillation column B which comprises a reaction zone C within the said distillation column B into three distinct product streams, one being a distillate (5) taken from the column head BH of column B which is rich in methylal, one stream (4) taken from the column bottom stream BB of column B being almost pure water, and one stream (3) taken from the side of the column B below the reaction zone C which stream is rich in methanol,
   optionally, feeding the product stream (5) taken from the column head BH of column B which consists almost exclusively of methylal, and further comprises a mass fraction of less than 10% of methanol to the side of a rectifying column D which is operated with a pressure which is higher than the pressure in column B, where a stream (7) comprising a mixture of methylal and methanol having a mass fraction of methylal of between 70% and 95% is recovered from the column top DH, and pure methylal is recovered as sump product stream (6) from the bottom DB of the column D, in a purity in excess of 99.5%, wherein
   the ratio of the amount of substance of methanol to the amount of substance of formaldehyde in the mixture M1 is at least 3 mol/mol, and
   the reaction of formaldehyde and methanol to form mixture M2 under at least partial formation of methylal and water is conducted in a the separate reactor A, and the mixture M2 from reactor A is fed to the side of the distillation column B to a feed point in a height corresponding to between 40% and 70% of the effective height of column B.

2. The process of claim 1, wherein in the first step, the reaction of formaldehyde and methanol to form mixture M2 under at least partial formation of methylal and water is conducted in a separate reactor A, and the mixture M2 is then fed to the side of the distillation column B which is additionally equipped with a reaction zone C which is located between the feed point and the bottom of the said column B, in which reaction zone at least partial conversion to methylal occurs.

3. The process of claim 1, wherein the reactor A is operated at a temperature between 40° C. and 80° C.

4. The process of claim 1, wherein the catalyst in reactor A is a fixed bed catalyst.

5. The process of claim 1, wherein the catalyst in reactor C is a fixed bed catalyst.

6. The process of claim 1, wherein a column D is used, and operated at a pressure which is at least 100 kPa higher than the pressure in column B, and where methylal is collected as sump product.

7. The process of claim 6, wherein the stream from the head DB of column D is recirculated to column B where it is fed to the side at a position of between 60% and 90% of the effective height of column B, but above the feed point of the mixture comprising methanol and formaldehyde or the mixture M2.

8. A reaction and purification apparatus for use in the process of claim 1, comprising
   a reaction vessel A equipped with a fixed bed catalyst,
   a distillation column B having two lateral feed inlets, and one lateral outlet, and a head and a sump outlet,
   a second distillation column D having one lateral feed inlet, and a head and a sump outlet.

9. The apparatus of claim 8, wherein the distillation column B has a reaction zone C equipped with a fixed bed catalyst.

10. The apparatus of claim 8, wherein the fixed bed catalyst comprises an ion exchange resin in its protonated form.

11. The apparatus of claim 8, wherein the reactor A is a tubular reactor.

* * * * *